United States Patent [19]

Margel et al.

[11] Patent Number: 4,552,812
[45] Date of Patent: Nov. 12, 1985

[54] PROCESS FOR THE PRODUCTION OF POLYACROLEIN MICROSPHERES AND GRAFTED MICROSPHERES

[75] Inventors: Shlomo Margel; Uzi Beitler, both of Rehovot, Israel

[73] Assignee: Yeda Research and Development Company, Rehovot, Israel

[21] Appl. No.: 330,451

[22] Filed: Dec. 14, 1981

[30] Foreign Application Priority Data

Jul. 1, 1981 [IL] Israel .................................. 63220

[51] Int. Cl.$^4$ .................. B32B 5/16; C08F 16/34; B01J 13/02; C12N 11/08
[52] U.S. Cl. ........................ 428/407; 260/513 B; 424/33; 424/85; 424/88; 424/94; 435/7; 435/180; 436/177; 436/501; 436/547; 427/213.34; 428/402.24; 523/223; 524/457; 525/54.1; 526/315; 526/909
[58] Field of Search .............. 252/316; 424/33; 524/457; 526/315, 909; 428/407, 402.24; 523/223; 427/213.34

[56] References Cited

U.S. PATENT DOCUMENTS

| | | | |
|---|---|---|---|
| 3,183,217 | 5/1965 | Serniuk et al. | 526/315 X |
| 3,824,114 | 7/1974 | Vassiliades et al. | 252/316 X |
| 4,003,846 | 1/1977 | Kuhn et al. | 252/316 |
| 4,046,720 | 9/1977 | Rembaum et al. | 526/312 X |
| 4,157,323 | 6/1979 | Yen et al. | 424/33 X |
| 4,267,235 | 5/1981 | Rembaum et al. | 428/407 |
| 4,269,821 | 5/1981 | Kreuter et al. | 424/33 X |
| 4,413,070 | 11/1983 | Rembaum | 523/223 |

OTHER PUBLICATIONS

Margel et al.: "Polyacrolein Microspheres as a New Tool in Cell Biology", J. Cell Science, vol. 56, pp. 157–175 (1982).
Kronick et al., "Magnetic Microspheres Prepared by Redox Polymerization . . .", Science, vol. 200, Jun. 2, 1978, pp. 1074–1076.
Ryder, Jr. et al.: "Polymerization of Acrolein by Redox Initiation", Journal of Polymer Science: Part A, vol. 3, pp. 3459–3469 (1965).
Pourfarzaneh et al.: "Composite Polyacrolein–Coated Cellulose Magnetizable Particles . . .", Clinica Chimica Acta III:61–63 (Mar. 1981).

*Primary Examiner*—Richard D. Lovering
*Attorney, Agent, or Firm*—John P. White

[57] ABSTRACT

Suspension polymerization of acrolein type compounds in the presence of appropriate surfactants results in the formation of microspheres in size ranging from 0.03$\mu$ to 80$\mu$. Fluorescent and magnetic microspheres are obtained by carrying out the same polymerization in the presence of appropriate fluorochromic or ferrofluidic compounds, respectively. Hybrido polyacrolein microspheres are obtained by grafting one type of such microspheres on another type. Immunomicrospheres were formed by binding covalently at physiological pH appropriate proteins to the microspheres. The immunomicrospheres can be used for various biological applications, such as specific markers for labelling cell surface receptors, for cell separation, for diagnostic purposes, etc.

25 Claims, 9 Drawing Figures

PROCESS FOR THE PRODUCTION OF POLYACROLEIN MICROSPHERES AND GRAFTED MICROSPHERES

FIELD OF THE INVENTION

The invention relates to a process for the production of microspheres from acrolein type compounds and to the thus prepared products. The microspheres may be fluorescent, magnetic and there can be prepared hybrido-microspheres. The microspheres are useful for various purposes such as cell labelling, cell separation, receptor separation, affinity chromatography, diagnostic purposes, enzyme immobilization, drug delivery and the like. The microspheres can be bound to various compounds having amino groups, such as drugs, enzymes, antibodies and antigens which retain their activity. The novel acrolein-type compound microspheres can be prepared by a variety of processes which are adjusted according to the desired product as regards diameter and other properties.

BACKGROUND OF THE INVENTION

There exists a great interest in the scientific community in developing a reliable technique for the isolation of cell surface receptors and for separating cells of various types. Labelling of specific receptors on cell surfaces has a great importance for understanding of various biological phenomena, such as cell-cell recognition in development, cell communication and differences between normal and tumor cell surfaces. Mapping of antigens and carbohydrate residues on the surface of cells has been studied intensively by various techniques, for example, using fluorescent (or radioactive) antibodies or lectins, or by binding biological macromolecules such as ferritin, hemocyanin, viruses and peroxidase to antibodies or lectins. The biological macromolecules were used as markers for transmission electron microscopy or for scanning electron microscopy (SEM). Polymeric microspheres were used also as markers for cell labelling. Polystyrene latex particles have been utilized as immunological markers for use in the SEM techniques. Such particles, because of their hydrophobic character, stick non-specifically to many surfaces and molecules and therefore limit their broad application. Many other types of polymeric microspheres which were hydrophilic were synthesized and were used for labelling cell surface receptors (Table 1).

TABLE 1 Classes of Hydrophilic Crosslinked Microspheres

1. Em class: methylmethacrylate (MMA) 2-hydroxyethylmethacrylate (HEMA), methacrylic acid (MA), and ethylene glycol dimethacrylate (EGDMA).[a]
2. L class: HEMA,MA,and bisacrylamide (BAM).[b]
3. BAH class: HEMA, acrylamide (AA),MA,and BAM.[b]
4. DMA class: HEMA, 2-dimethylaminoethylmethacrylate (DMA),and BAM.[b]
5. PVP class: 4-vinyl pyridine alone or with HEMA and/or AA.[b]

[a] Emulsion polymerization
[b] Cobalt gamma radiation

The labelling procedure was carried out by using either the direct or the indirect methods (FIG. 1).

In both methods the first step requires the covalent binding of a purified antibody to a microsphere through the functional groups on its surface. In the direct method the immunomicrospheres (microspheres to which specific antibody is covalently bound) seek out the cell antigens and bind to it, and in the indirect method an intermediate antibody is employed.

The microspheres, depending on the initial monomer composition, had either carboxyl, hydroxyl, amide and/or pyridine groups on their surface. The functional groups were used to covalently bind antibodies and other proteins to the microspheres by using either the cyanogen bromide, carbodiimide, or glutaraldehyde methods (FIGS. 2 and 3).

The last step of the microspheres derivatization technique, prior to protein binding, consisted of a reaction with glutaraldehyde, designed to introduce reactive aldehyde groups on the surface of the beads.

Recently, a patent application was filed by A. Rembaum and S. Margel describing a method for preparation of polyglutaraldehyde microspheres U.S. Ser. No. 21,988, filed Mar. 19, 1979, and now U.S. Pat. No. 4,267,235. These polyaldehyde microspheres were used for binding in a single step appropriate proteins at physiological pH.

SUMMARY OF THE INVENTION

The present invention relates to a novel synthesis of polyacrolein microspheres, homo and hydrido microspheres and to their biological potential uses.

Polyacrolein Microspheres

Polyacrolein microspheres were prepared in two ways:

(a) polymerization of acrolein under basic conditions in the presence of appropriate surfactants-anionic microspheres; and (b) radical polymerization of acrolein in the presence of appropriate surfactants, without or in presence of other acrylic monomers, radicalic microspheres.

(a) Basic Conditions

Polymerization of acrolein, in aqueous media under basic conditions, results in the formation of the water insoluble polyacrolein polymer. The polymerization is first order related to acrolein concentration and the rate is dependent on the pH of the polymerization (FIG. 4)—the higher the pH, the faster the polymerization. Analysis by IR spectroscopy confirms the presence of aldehyde groups as well as hydroxyl groups, carboxyl groups, ether groups and double bonds. At very high pH (higher than 13.5), due to Cannizzaro reaction, (two aldeyde groups react to give one hydroxyl group and one carboxyl group) a water soluble polyacrolein is obtained.

Anionic Polyacrolein Microspheres

Polymerization of acrolein, in aqueous media under basic conditions and in the presence of appropriate surfactants (ionic, i.e. anionic and cationic), results in the formation of polyacrolein microspheres (FIG. 5). The size of the microspheres can be controlled by changing either the acrolein concentration (FIG. 6), surfactant concentration (FIG. 7) or pH of the polymerization (FIG. 8). Addition of dimethylformamide to the aqueous medium (or other correlated solvents e.g. dimethyl-sulfoxide) increases the solubility of acrolein and results in the formation of uniform large polyacrolein beads.

Fluorescent or magnetic microspheres were obtained by carrying out the acrolein polymerization in the presence of appropriate fluorochromic (e.g. fluorescein isothiocyanate, aminofluorescein, tetramethyl rhodamine isothiocyanate, etc) or ferrofluidic compounds, respectively.

(b) Radical Polymerization of Acrolein

Polymerization of acrolein in aqueous media was carried out by using redox initiators, such as ammonium persulfate-silver nitrate, or cobalt radiation (Coy). The structure of the polyacrolein obtained in a simplified form is

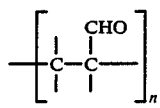

where n is an integer of 100 to 10,000, and it is different from that obtained by the basic polymerization. The hydrophilicity (and therefore the specificity towards cells) of the polyacrolein, obtained by the radical polymerization, can be increased by either stirring the polymer at a high pH (approximately pH 12) of an aqueous solution (due to Cannizzaro reaction) or by copolymerizing acrolein with hydrophilic monomers (such as hydroxy methyl-methacrylate).

Radical Polyacrolein Microspheres

Radical polymerization of acrolein, in the presence of appropriate surfactants, results in the formation of the radical microspheres (which have a different structure than that obtained by the basic polymerization.) Increasing the pH (of the suspension solution) to a value between 11.5 to 13 will increase the hydrophilicity of these microspheres. Copolymerization of acrolein with hydrophilic monomers, in the presence of appropriate surfactants, also produces more hydrophylic microspheres.

HYBRIDO MICROSPHERES

The anionic polyacrolein microspheres have been coated with the radicalic microspheres (FIG. 9). The relatively large anionic microspheres are completely covered with the smaller radical beads, e.g. $2.0\mu$ anionic beads are covered with $0.1\mu$ radical beads. However, increasing the size of the radical microspheres to $0.5\mu$ will cause the radical beads to detach from the surface of the anionic microspheres. The coating procedure is based on the radical polymerization of acrolein in the presence of the anionic microspheres. The mechanism of the coating involves the grafting of the radical microspheres onto the surface of the anionic beads through their double bonds.

Based on this grafting technique the anionic polyacrolein microspheres had been coated with may other types of polymeric microspheres, e.g. polyvinylpyridine microspheres ($0.2\mu$ diameter) were grafted on the surface of the anionic polyacrolein beads ($2\mu$ diameter) by carrying out the radical polymerization of 4-vinylpyridine in the presence of the anionic polyacrolein beads.

DESCRIPTION OF THE PREFERRED EMBODIMENT

The invention is illustrated with reference to the enclosed Figures in which:

FIG. 9A illustrates $2.0\mu$ average anionic polyacrolein microspheres coated with $0.1\mu$ radicalic polyacrolein microspheres ($\times 4600$).

FIG. 9B illustrates $2.0\mu$ anionic polyacrolein microspheres coated with 0.1 radicalic polyacrolein microspheres ($\times 12000$).

EXAMPLE 1

Synthesis of the surfactant -PGL-NaHSO$_3$

Figure 1:
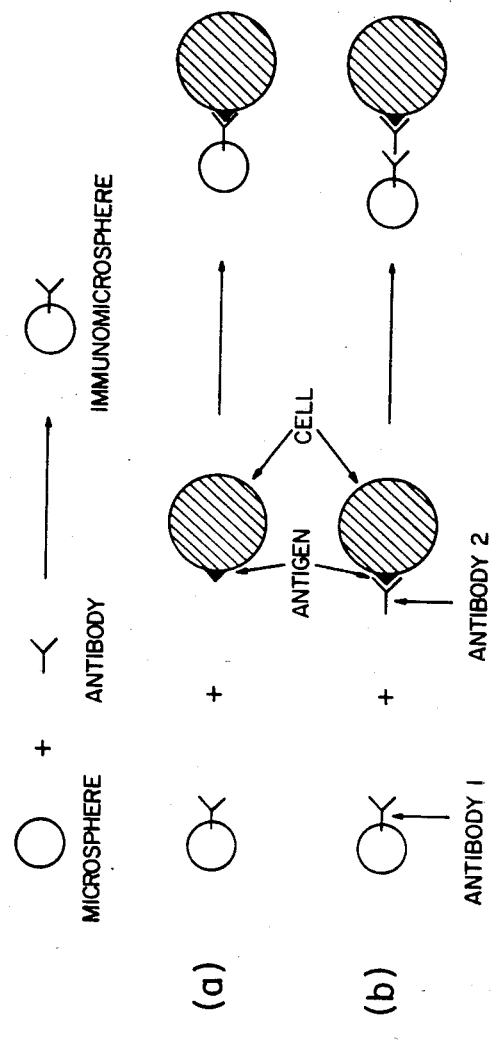
FIG. 1 is a schematic representation of direct (a) and indirect (b) labelling of living cells by means of immunomicrospheres.
Figure 2:
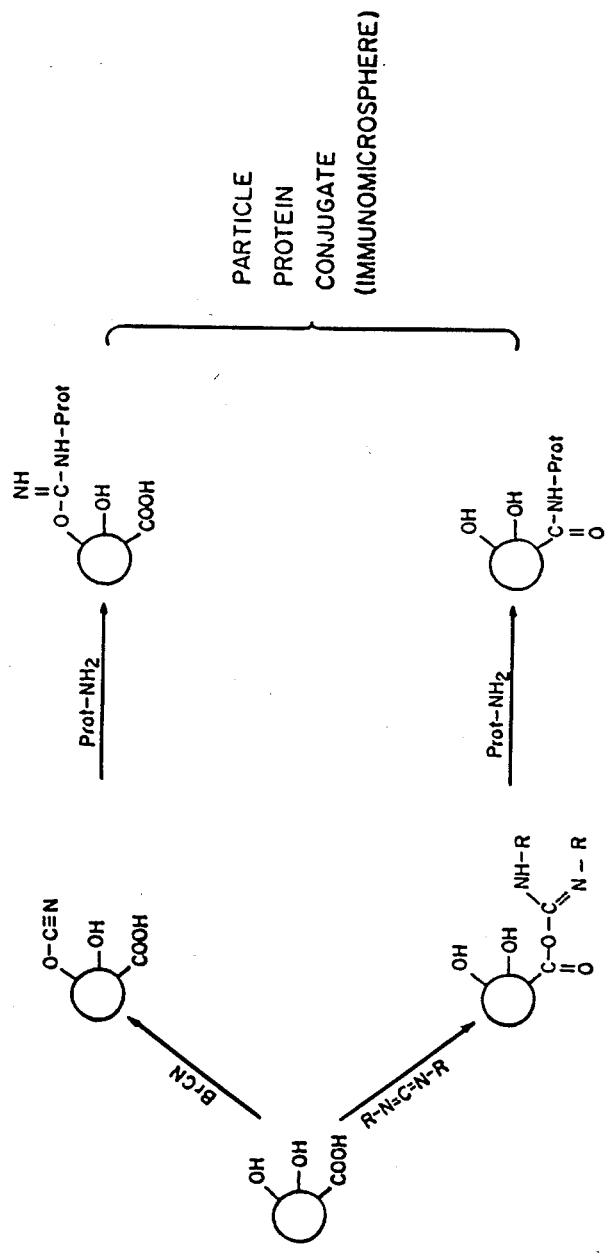
FIG. 2 is a reaction scheme for the cyanogen bromide and the carbodiimide procedures.
Figure 3:
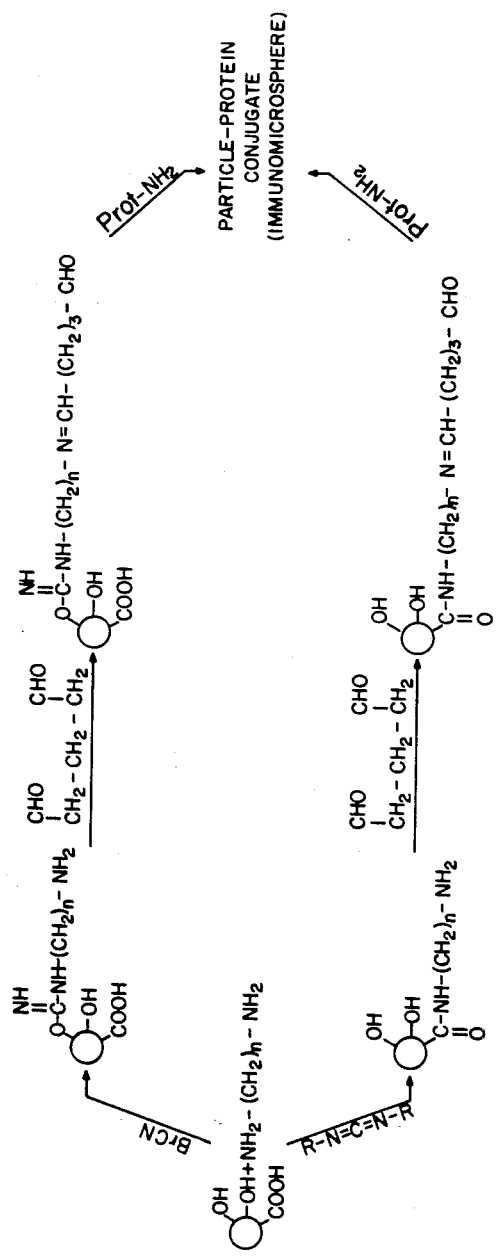
FIG. 3 is a reaction scheme for the glutaraldehyde procedure.
Figure 4:
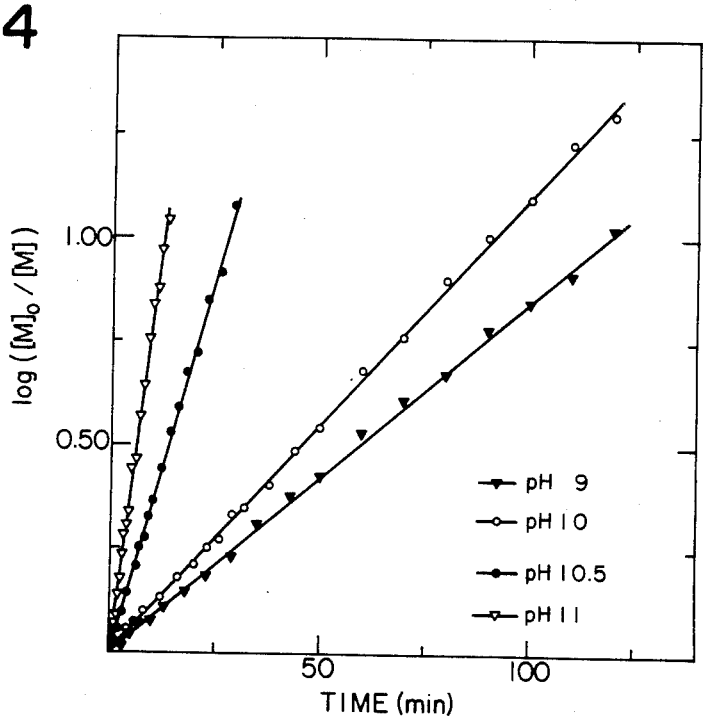
FIG. 4 illustrates first-order rate plates, at various pH's for acrolein polymerization in aqueous media (temp. 23° C., acrolein concentration 2%)
Figure 6:
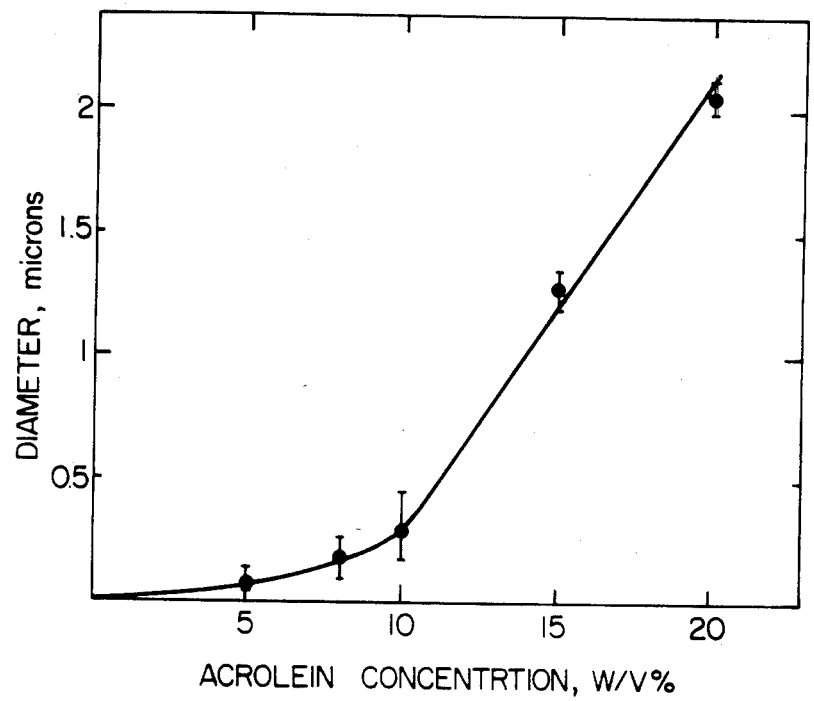
FIG. 6 illustrates size of polyacrolein microspheres as a function of acrolein concentration (temp. 23° C., pH 10, surfactant (PGL-NaHSO$_3$) 0.5% w/v)
Figure 5:
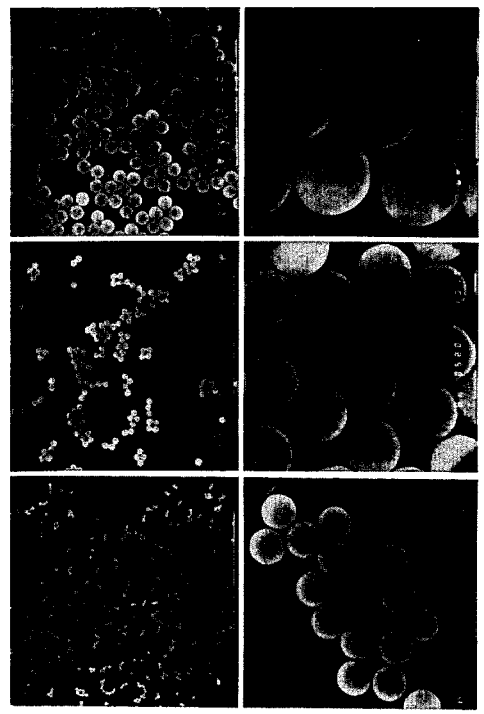
FIG. 5 illustrates scanning electron microscopy photomicrographs of polyacrolein microspheres of various sizes.
Figure 7:
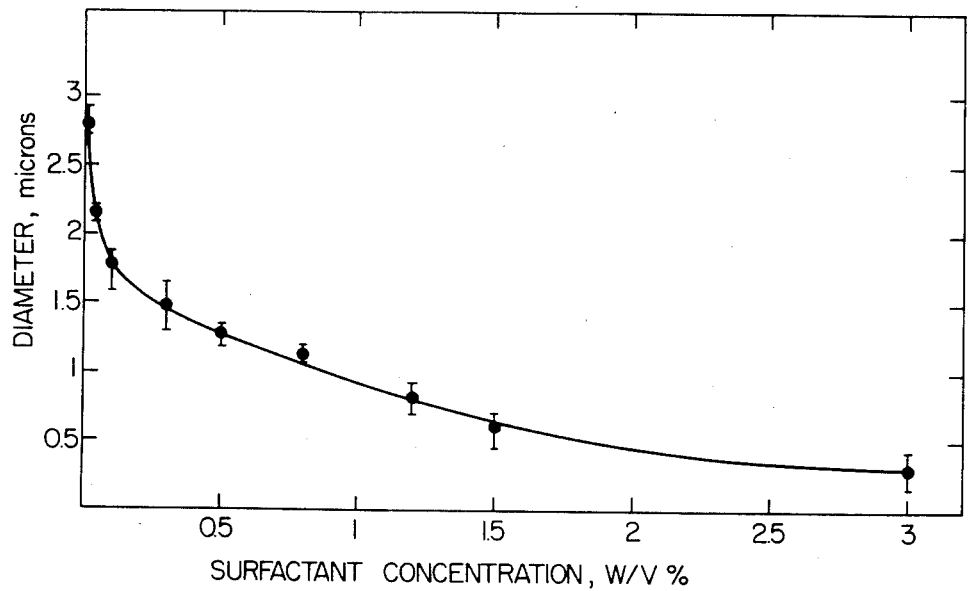
FIG. 7 illustrates size of polyacrolein microspheres as a function of surfactant (PGL-NaHSO$_3$) concentration (temp. 23° C. pH 10, acrolein 15% w/v)
Figure 8:
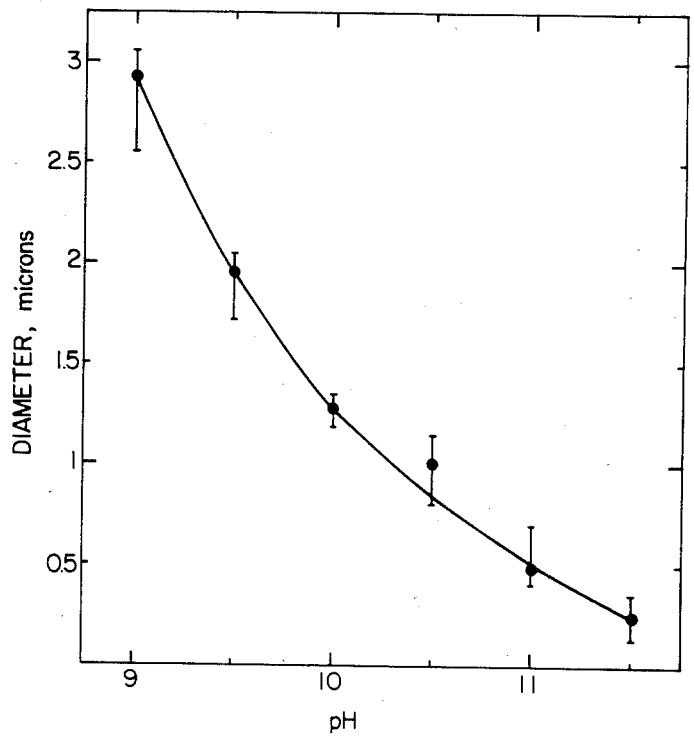
FIG. 8 illustrates size of polyacrolein microspheres as a function of pH polymerization (temp. 23° C., acrolein 15% w/v, surfactant (PGL-NaHSO$_3$) 0.5% w/v).

This surfactant was prepared by the reaction of polyglutaraldehyde (PGL) and sodium hydrogen sulfite (NaHSO$_3$), as follows: 12.5 g NaHSO$_3$ were dissolved in 30 ml H$_2$O. 5 g of PGL was then added and the solution was stirred until all the PGL was dissolved. The solution was dialysed extensively against H$_2$O (molecular weight cutoff of the dialysing bag was 3,500), and then lyophilized.

EXAMPLE 2

Formation of Polyacrolein Microspheres under Basic Conditions 0.2 N aqueous NaOH solution was added dropwise to a solution containing 8% w/v acrolein and 0.5% of the surfactant PGL-NaHSO$_3$ until pH 10.5 was reached. The reaction was continued for 2 hours, and the produced microspheres (diameter $0.1\mu$) were then washed four times by centrifugation at $2000 \times g$ for 20 minutes. By varying the surfactant and/or the acrolein concentration, the pH of polymerization or the solvent, the size of the microspheres can be changed in a predictable way.

EXAMPLE 3

Magnetic Microspheres

Example 2 was repeated in the presence of 5% (v/v) of a ferrofluidic solution (aqueous dispersion of Fe$_3$O$_4$, sold by Ferrofluidics, Burlington, Mass., No. A01 5% w/v) and resulted in the formation of magnetic polyacrolein microspheres of average size of $0.04\mu$. The magnetic microspheres were washed by dialysis and then separated from diamagnetic impurities by means of a permanent magnet.

EXAMPLE 4

Fluorescent Microspheres

Example 2 was repeated in the presence of 0.008% tetramethyl rhodamine isothiocyanate and resulted in the formation of 0.1μ diameter fluorescent polyacrolein microspheres.

EXAMPLE 5

Example 2 was repeated in the presence of methacrolein (instead of acrolein). Microspheres in average size of 0.1μ were produced.

EXAMPLE 6

Example 2 was repeated in the presence of crotonaldehyde (instead of acrolein). Microspheres in average size of 0.2μ were obtained.

EXAMPLE 7

The procedure of Example 2 was repeated substituting the surfactant PGL-NaHSO$_3$ by the anionic surfactants Dowfax 2A1 (or Dowfax 3B2). There were obtained polyacrolein microspheres in average size of 0.1μ.

EXAMPLE 8

The procedure of Example 2 was repeated substituting the surfactant PGl-NaHSO$_3$ with the non-ionic surfactant Polysurf 10-36B (based on a copolymer of acrylamide and isobutoxy acrylamide, provided by Bartig Industries, Inc., Birchwood Ave, New Canaan, Conn. 06840 U.S.A.). No polyacrolein microspheres were obtained by this process.

EXAMPLE 9

0.2 N aqueous was added dropwise to an aqueous solution containing 10% dimethyl formamide 25% (w/v) acrolein and 0.08% (w/v) of the surfactant PGL-NaHSO$_3$ unit pH 11.5 was reached. The reaction was continued for an hour and then the produced monodispersed microspheres 3μ diameter) were washed 4 times by spinning at 500×g for 10 minutes.

EXAMPLE 10

10 ml of an aqueous solution containing 10% (w/v) dimethyl formamide and 0.3% (w/v) of the surfactant PGL-Na-HSO$_3$ was brought to pH 11.2. The solution was stirred gently and 5 ml of acrolein was added. The reaction continued for 15 minutes and the produced beads (average size of 80μ) were washed several times by decantation.

EXAMPLE 11

Formation of Polyacrolein Microspheres under Radical Conditions 100 ml of an aqueous solution containing 9% (w/v) acrolein and 0.5% (w/v) polyethylene oxide (m.w. 100,000) was deaerated with argon and radiated then with cobalt source (1 Mega rad). The produced microspheres (0.15μ size) were washed by centrifugation 4 times at 2000×g for 30 minutes.

EXAMPLE 12

Example 11 was repeated in the presence of 5% (w/v) of hydroxy methyl methacrylate. Microspheres in average size of 0.2μ were obtained.

EXAMPLE 13

Example 11 was repeated in the presence of 1% (w/v) N.N'-methylene-bis-(acrylamide) as cross linker. Microspheres in average size of 0.15μ were obtained.

Example 14

Example 11 was repeated in the presence of methacrolein. Microspheres in average size of 0.2μ were obtained.

EXAMPLE 15

Example 14 was repeated in the presence of 0.008% (w/v) of fluorescein isothiocyanate and resulted in the formation of 0.2μ fluorescent polymethacrolein microspheres.

EXAMPLE 16

Example 11 was repeated in the prescence of methyl vinyl ketone. Microspheres in average size of 0.2μ were obtained.

EXAMPLE 17

The microspheres prepared as in Example 11 were treated for 12 hours in a basic aqueous solution (pH 12.0) and then washed four times by spinning at 2000×g for 30 minutes. The hydrophilic microspheres obtained had an average size of 0.15μ.

EXAMPLE 18

120 ml of an aqueous solution containing 9% (w/v) acrolein, 0.5% (w/v) polyethylene oxide (m.w. 100,000) and 1.0 mmol of ammonium persulfate was deaerated with argon. 1.0 mmol of AgNO$_3$ was then added to the stirred solution. The reaction continued for 12 hours and the produced beads with average size of 0.1μ were washed 4 times by spinning at 2000×g for 20 minutes.

EXAMPLE 19

Example 18 was repeated in the presence of 5% (v/v) of ferrofluid solution and resulted in the formation of magnetic polyacrolein microspheres of average size of 0.05μ. The magnetic microspheres were washed by dialysis and then separated from diamagnetic impurities by means of a permanent magnet.

EXAMPLE 20

Figure 9:
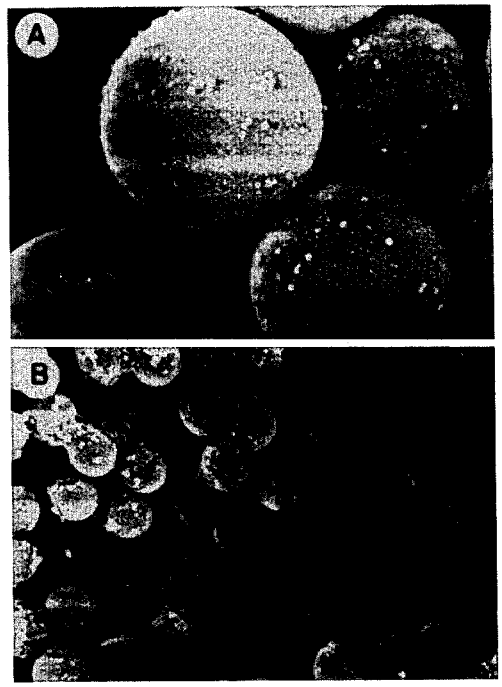
FIG. 9 illustrates scanning electron microscopy photomicrographs of hybrido polyacrolein microspheres.

Formation of Hybrido Microspheres 4 ml of an aqueous solution containing 9% (w/v) acrolein, 0.5% (w/v) polyethylene oxide (m.w. 100,000) and 100 mg of the anionic polyacrolein beads of 2.0μ size was deaerated with argon. The stirred solution was then radiated with cobalt source (1 mega rad). The grafted microspheres (FIG. 9) were washed from excess of 0.1μ radical microspheres by spinning four times at 500×g for 10 minutes.

EXAMPLE 21

4 ml of an aqueous solution containing 8% (w/v) acrolein, 0.5% (w/v) polyethylene oxide (m.w. 100,000), 0.06 mmol of ammonium persulfate and 100 mg of the anionic polyacrolein beads of 2.0μ size was deaerated with argon to the stirred solution 0.06 milimole of AgNO$_3$ was then added. The reaction continued for 12 hours and the grafted microspheres were washed by centrifugation 4 times at 500×g for 10 minutes.

EXAMPLE 22

The procedure of example 20 was repeated substituting acrolein with 1% (w/v) 4-vinyl pyridine.

EXAMPLE 23

The procedure of example 21 was repeated substituting acrolein with 1% (w/v) 4-vinyl pyridine.

EXAMPLE 24

Labelling of Red Blood Cells with Microspheres

Polyacrolein microspheres obtained by basic polymerization were shaken for 2 hours, at 4° C., with purified goat anti rabbit IgG (GxRIgG) (1 mg microspheres, 0.1 mg GxRIgG in total volume of 0.15 ml PBS). Thereafter unbound antibody was separated by passing the microsphere suspension through a Sepharose 4B column. The separation was monitored spectrophotometrically at $A \times 280$ nm. The free aldehyde groups of the conjugate microspheres antibody were quenched with 2% (w/v) bovine serum albumin solution for several hours at 4° C.

Fresh human RBC, from a normal donor, were shaken for 50 min at 4° C. with rabbit anti human RBC (Cappel Lab. Inc.) ($10^6$ human RBC with 0.8 $\mu$g rabbit against human RBC in 0.1 ml PBS solution). The sensitized cells were separated and washed 4 times by spinning the cells suspension in an international centrifuge at $500 \times g$. The goat anti rabbit derivatized microspheres were then added to the sensitized human RBC and the mixture was shaken at 4° C. for 1 hour. The RBC were separated from unreacted derivatized microspheres by centrifugation 3 times at $500 \times g$. The labelled cells were resuspended in PBS and were examined in light fluorescent microscopy and with fluorescence-activated cell sorter (FACS-11 (Becton-Dickinson - photomultiplier 600V, 2 filters - 550 nm).

EXAMPLE 25

Separation of turkey RBC from human RBC

A mixture containing $10^6$ human RBC and $10^6$ turkey RBC was treated with magnetic microspheres by using the former labelling procedure. Then a small magnet was fitted on the outside wall of a vial containing PBS solution of the cells mixture. After 10 minutes, cells which were not attracted to the wall were isolated. The attracted cells were resuspended with PBS and the magnetic separation was repeated twice. Examination with light microscopy showed that more than 90% of the attracted cells were human RBC.

Polyacrolein microspheres can be used for cell labelling and cell separation of other systems (e.g. labelling and separation of B and T cells) as well as for other purposes such as drug delivery, enzyme immunoassay, and enzyme mobilization.

We claim:

1. A process for producing a polyacrolein-type microsphere which comprises subjecting an aqueous mixture of a polymerizable acrolein-type monomer to polymerization in the presence of an effective amount of a suitable ionic surfactant which promotes microsphere formation upon polymerization of the monomer so as to form a microsphere, the polymerization being effected at a pH between 8.0 and 13.7, and recovering the resulting microsphere and purifying the microsphere so recovered.

2. A process according to claim 1, wherein acrolein-type compound is acrolein, methacrolein or crotonaldehyde.

3. A process according to claim 1, wherein the effective amount of the surfactant is an amount from about 0.02 to 0.03 percent by weight based upon the volume of the mixture.

4. A process according to claim 1, wherein the surfactant is anionic.

5. A process according to claim 1, wherein the acrolein-type compound is acrolein and the surfactant is PGL-NaHSO$_3$.

6. A process according to claim 1, wherein the mixture contains an additional solvent.

7. A process according to claim 6, wherein the additional solvent is N,N-dimethylformamide.

8. A process according to claim 1, wherein sodium hydroxide is added to the mixture to obtain the pH between 8.0 and 13.7.

9. A process according to claim 1, wherein the mixture additionally contains a fluorescent dye.

10. A process according to claim 1, wherein the mixture additionally contains a ferrofluidic material.

11. A process according to claim 10, wherein the ferrofluidic material is Fe$_3$O$_4$.

12. A grafted microsphere comprising a polyacrolein microsphere to which at least one polymeric microsphere having a diameter less than one-fourth the diameter of the polyacrolein-type microsphere is attached, wherein the larger polyacrolein-type microsphere is produced according to claim 1.

13. A process for producing a polyacrolein-type microsphere which comprises subjecting under an inert atmosphere and suitable conditions an aqueous mixture of a polymerizable acrolein-type monomer to polymerization in the presence of an effective amount of a suitable surfactant which promotes microsphere formation upon polymerization of the monomer, an oxidizing agent and a reducing agent, the oxidizing agent and reducing agent both being present in amounts capable of initiating a redox reaction so as to effect polymerization of the acrolein-type monomer and microsphere formation, recovering the resulting microsphere and purifying the microsphere so recovered.

14. A process according to claim 13, wherein the oxidizing agent is ammonium persulfate and the reducing agent is silver nitrate.

15. A process according to claim 13, wherein the acrolein-type compound is acrolein, methacrolein or crotonaldehyde.

16. A process according to claim 13, wherein the effective amount of the surfactant is an amount from about 0.02 to 3.0 percent by weight based upon the volume of the mixture.

17. A process according to claim 13, wherein the acrolein-type compound is acrolein and the surfactant is polyethylene oxide.

18. A process according to claim 13, wherein the mixture contains an additional solvent.

19. A process according to claim 13, wherein the mixture additionally contains an acrylate monomer.

20. A process according to claim 13, wherein the reaction mixture additionally contains a fluorescent dye.

21. A process according to claim 13, wherein the mixture additionally contains a ferrofluidic material.

22. A process according to claim 21, wherein the ferrofluidic material is Fe$_3$O$_4$.

23. A grafted microsphere comprising a polyacrolein-type microsphere to which at least one polymeric microsphere having a diameter less than one-fourth the diameter of the polyacrolein-type microsphere is attached.

24. A grafted microsphere according to claim 23, wherein the larger polyacrolein-type microsphere is polyacrolein and the smaller polymeric microsphere is polyacrolein, poly-2-vinyl pyridine or poly-4-vinyl pyridine.

25. A grafted microsphere according to claim 24, wherein the smaller polymeric microsphere is polyacrolein.

* * * * *

UNITED STATES PATENT AND TRADEMARK OFFICE
CERTIFICATE OF CORRECTION

PATENT NO. : 4,552,812

DATED : November 12, 1985

INVENTOR(S) : Shlomo Margel and Uzi Beitler

It is certified that error appears in the above-identified patent and that said Letters Patent is hereby corrected as shown below:

Col. 3, line 59, "0.2" should read --0.1--.

Col. 5, line 4, after "0.008%" insert --(w/v)--.

Col. 5, line 29, "PG1-NaHSO3" should read --PGL-NaHSO$_3$--.

Col. 5, line 37, after "0.2 N aqueous" insert --NaOH--.

Col. 5, line 48, "PGL-Na-HSO$_3$" should read --PGL-NaHSO$_3$--.

Col. 7, line 20, "Ax280" should read --A=280--.

Col. 8, line 6, "0.03" should read --3.0--.

Signed and Sealed this

Eighth Day of April 1986

[SEAL]

Attest:

DONALD J. QUIGG

Attesting Officer

Commissioner of Patents and Trademarks